United States Patent [19]
Matsuura et al.

[11] Patent Number: 5,615,007
[45] Date of Patent: Mar. 25, 1997

[54] METHOD OF DETECTING CRACK AND CHIP IN FLANGE OF SYRINGE

[75] Inventors: Yoshimasa Matsuura, Honjo; Mikio Tagaya; Ryosaku Tagaya, both of Isesaki, all of Japan

[73] Assignee: Eisai Co., Ltd., Tokyo, Japan

[21] Appl. No.: 443,015

[22] Filed: May 17, 1995

[30] Foreign Application Priority Data

May 20, 1994 [JP] Japan .................................... 6-106785

[51] Int. Cl.$^6$ ................................................. G01N 21/00
[52] U.S. Cl. .............................................. 356/237; 356/239
[58] Field of Search .................................. 356/237, 239, 356/240, 429, 430; 250/559.42, 559.43; 348/127; 414/416, 751

[56] References Cited

U.S. PATENT DOCUMENTS

| | | | |
|---|---|---|---|
| 3,085,160 | 4/1963 | Dahms | 356/237 |
| 3,782,836 | 1/1974 | Fey et al. | 356/237 |
| 4,547,073 | 10/1985 | Kugimiya | 356/237 |
| 4,606,635 | 8/1986 | Miyazawa et al. | 356/240 |
| 4,697,076 | 9/1987 | Yoshida | 356/240 |
| 5,268,735 | 12/1993 | Hayashi | 356/237 |

*Primary Examiner*—Hoa Q. Pham
*Attorney, Agent, or Firm*—Griffin, Butler Whisenhunt & Kurtossy

[57] ABSTRACT

A light is illuminated, for example, from the side of a flange of a syringe. An imaging processing is carried out with an image signal issued by imaging a reflected light from the edge of flange by means of a TV camera or CCD camera located, for example, in an upward slant direction. Detecting an irregular state of the image signal caused by the reflected light, a crack or chip at the flange are recognized. The irregular state of the image signal, which is obtained by detecting parts where the light is not reflected, brings the method of being easy to detect the crack or chip at the flange.

3 Claims, 3 Drawing Sheets

METHOD OF DETECTING CRACK AND CHIP IN FLANGE OF SYRINGE

BACKGROUND OF THE INVENTION

1. Field of the Invention

The present invention relates to a method of detecting a crack or chip at a flange of a syringe.

2. Description of the Related Art

Japanese Patent Application Laid-open No. Hei01-150848 discloses a bottle's mouth inspection method of deciding whether a bottle's mouth portion is in a normal state or not by the steps of: illuminating light to the bottle's mouth portion; carrying out an image processing based on a camera signal issued by imaging a reflected light caused by the illuminated light; measuring the trace of a shape by an image signal informing halation by a twist; and measuring the trace of the shape with the trace of the shape meeting the standard.

"Method of inspecting flaw in mouth portion" of Japanese Patent Application Laid-open No. Sho63-277960 and "Method of inspecting appearance of bottle's mouth" of Japanese Patent Application Laid-open No. Hei05-157707 are known as a method of inspecting an appearance of the bottle.

However, the above-mentioned methods are not for detecting a crack or chip at a flange of a syringe. Conventionally, there has been no method of detecting with certainty and automatically a crack or chip at the flange shape part of the syringe.

SUMMARY OF THE INVENTION

It is an object of the present invention to obtain a method of detecting a crack or chip at a flange of a syringe.

To attain the above-mentioned object, the present invention provides the method of detecting the crack or chip at the flange of the syringe.

Concretely, the method of detecting the crack or chip at the flange of the syringe as a technical means to attain the above-mentioned object is provided in the steps of: illuminating a light from the side of the flange of the syringe; carrying out an image processing based on an image signal issued by imaging a reflected light from an edge of the flange by means of a TV camera or CCD camera located, for example, in an upward slant direction; and ascertaining whether the flange of the syringe has a crack or chip by detecting an irregular state of the image signal caused by the reflected light.

Results of the present invention are that the detecting method is be simple and the quality of the syringe can be accurately ascertained because the flange of the syringe is illuminated from the side by the light and the crack or chip at the flange is detected through the image processing based on the reflected light from the edge of flange, which is caused by the illuminating light.

BRIEF DESCRIPTION OF THE DRAWINGS

The above and other objects of the invention will be seen by reference to the description taken in connection with the accompanying drawings, in which.

DETAILED DESCRIPTION OF THE PREFERRED EMBODIMENT(S)

A preferred embodiment of the present invention will be explained in accordance with the attached drawings.

Figure 4:
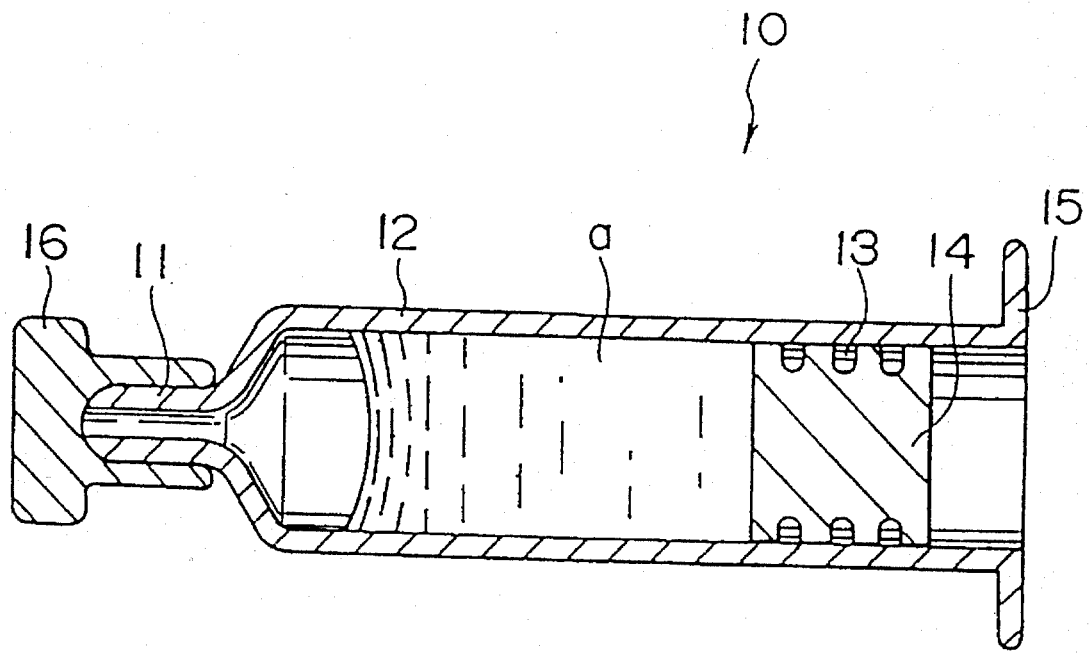
FIG. 4 is a front view, partly in cross section, of the structure of the syringe in FIG. 1.

As shown in FIG. 4, a syringe (10) has a structure which a plunger (14) including a ring groove (13) formed to prevent liquid from leaking is inserted in an outer casing (12) having a nozzle (11) to be attached to a needle and a flange (15) is formed at the rim of the opened end of the outer casing (12) to fit a rod of a pushing plunger member therein. The outer casing (12) is injected therein with drug (a) and the nozzle (11) receives a cap (16).

After the needle, which is attached to the nozzle (11) after taking off the cap (16), is stuck in a body to a predetermined depth, a predetermined quantity of drug (a) in the syringe is injected into the body through the needle by means of the plunger pushed by the rod of the pushing plunger member.

The present invention relates to a method of detecting a crack or chip produced at the flange (15) of the syringe (10) as described above in order to maintain the quality of the syringe.

Figure 1:
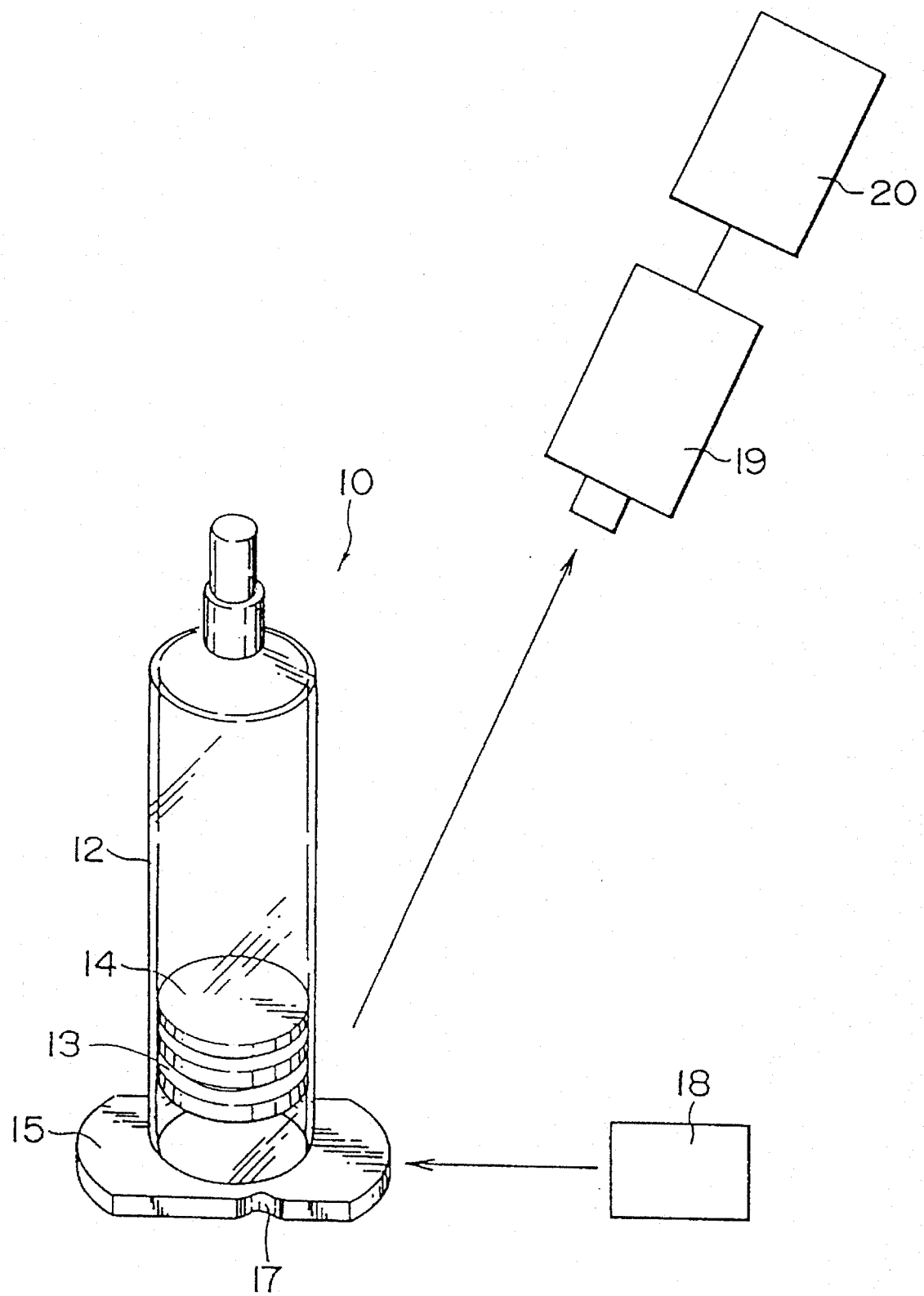
FIG. 1 is a perspective view of an outline for a detecting method according to the present invention.

As shown in FIG. 1, the flange (15) of the syringe (10), which has the chip (17), is put on a rotating table (not shown), illuminated by a light from a light source (18) toward the side of the flange (15) while the table rotates, and imaged with reflected light from the edge of the flange (15) by means of a TV camera (19) located in an upward slant direction of the flange (15). An image signal issued by imaging as stated above causes an image processing device (20) to carry out an image processing so as to obtain the image as shown in FIG. 2.

Figure 2:
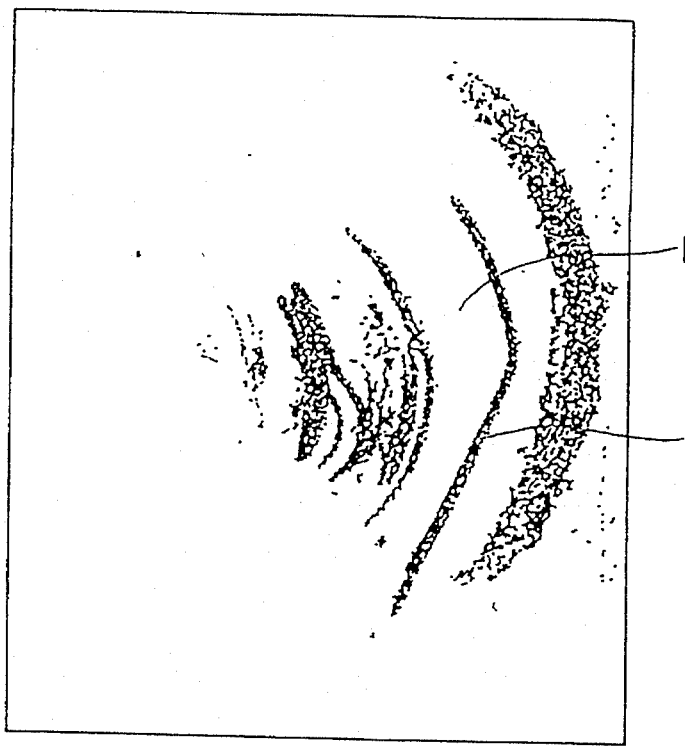
FIG. 2 is a diagram of an image processing in the complete state of a flange of a syringe in FIG. 1.
Figure 3:
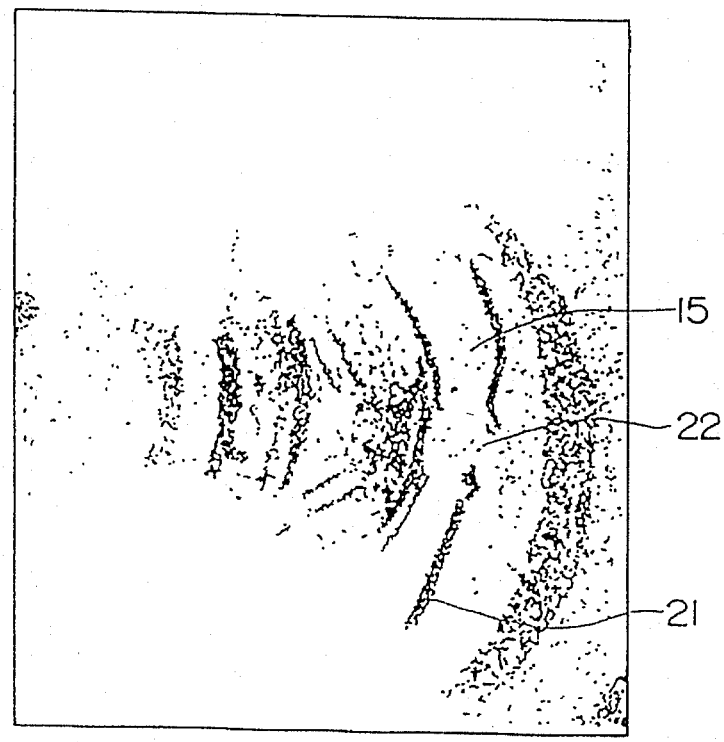
FIG. 3 is a diagram of the image processing in the incomplete state of the flange of the syringe in FIG. 1 because of a chip.

As a result, if a lighted part (21) showing a lighted state of the reflected light from the flange (15) in FIG. 2 is disturbed into more than two paths (22) as shown in FIG. 3, it can be recognized that the flange (15) has the chip (17). The lighted part (21) is shown in white and the other is shown in black on an actual screen, but FIG. 2 is indicated in the reverse state of white and black.

Incidentally, the syringe (10) is secured on the rotating table and the circumference of the syringe (10) can be inspected by rotating the rotating table.

When the lighted part (21) is not disturbed, it is understood that the syringe (10), as shown in FIG. 2, dose not have any chip.

However, as shown in FIG. 3, black parts (they are white on the drawing but black on the actual screen.) mean parts where the light is not reflected to the TV camera. The light which illuminates the chip (17) on the edge of the flange (15) and the surface of the flange cannot reflect light to the TV camera, for the flange (15) is illuminated from the side by the light.

Consequently, the above-mentioned method can ascertain whether the syringe has the crack or chip or not.

In the embodiment, tile TV camera or CCD camera and the light source are located in the same side to be able to utilize the reflected light. However, there may be a plurality of locations of TV cameras and light sources for obtaining reflected light from the edge of the flange.

Whichever method is taken, it is characteristic of the present invention to ascertain whether the syringe has the crack and chip by being illuminated from the side and toward the flange of the syringe, carrying out tile image processing based on the image signal issued by imaging the reflected light by means of the TV camera or CCD camera located in the upward slant direction and detecting the irregular state of the imaging signal caused by the reflected light.

While the present invention has been particularly shown and described with reference to preferred embodiment thereof, it will be understood by those skilled in the art that the foregoing and other changes in form and details can be made therein without departing from the spirit and scope of the invention.

What is claimed is:

1. A method for detecting a crack or chip at a flange of a syringe, comprising:

(1) illuminating a side edge of the flange with light from a light source which directs the light toward the side edge of the flange such that the side edge reflects light in an upwardly slanted direction;

(2) producing image signals with a camera responsive to the side edge reflected light, said camera being located so as to receive the light reflected in the upwardly slanted direction;

(3) receiving the image signals in an image processing device and processing the signals to display a corresponding image; and (4) determining the absence or existence of a crack or chip by monitoring the displayed image for disturbed image patterns wherein the crack or chip at the flange is recognized by an absence of reflected light.

2. A method of detecting a crack or chip at a flange of a syringe according to claim 1, wherein the flange of the syringe is rotated.

3. A method of detecting a crack or chip at a flange of a syringe according to claim 1, wherein the camera is a TV camera or a CCD camera.

* * * * *